US011301772B2

(12) United States Patent
Ito et al.

(10) Patent No.: US 11,301,772 B2
(45) Date of Patent: Apr. 12, 2022

(54) MEASUREMENT, ANALYSIS AND APPLICATION OF PATIENT ENGAGEMENT

(71) Applicant: International Business Machines Corporation, Armonk, NY (US)

(72) Inventors: Marcia Ito, Sao Paulo (BR); Gabriel Do Nascimento Ribeiro, Sao Paulo (BR)

(73) Assignee: International Business Machines Corporation, Armonk, NY (US)

( * ) Notice: Subject to any disclaimer, the term of this patent is extended or adjusted under 35 U.S.C. 154(b) by 1206 days.

(21) Appl. No.: 15/066,144

(22) Filed: Mar. 10, 2016

(65) Prior Publication Data

US 2017/0262950 A1 Sep. 14, 2017

(51) Int. Cl.

| | |
|---|---|
| ***G06N 20/00*** | (2019.01) |
| ***G06F 16/35*** | (2019.01) |
| ***G06F 16/33*** | (2019.01) |
| ***G16H 40/20*** | (2018.01) |

(52) U.S. Cl.

CPC ......... *G06N 20/00* (2019.01); *G06F 16/3344* (2019.01); *G06F 16/35* (2019.01); *G16H 40/20* (2018.01)

(58) Field of Classification Search

CPC ... G06Q 50/22; G06F 19/00; G06F 17/30705; G06F 17/30684; G06F 16/3344; G06F 16/35; G06N 99/005; G06N 20/00; G16H 40/20

USPC ........................................................ 705/2, 3

See application file for complete search history.

(56) References Cited

U.S. PATENT DOCUMENTS

| | | | |
|---|---|---|---|
| 8,412,542 | B2 | 4/2013 | Mok |
| 2005/0108051 | A1 | 5/2005 | Weinstein |
| 2007/0015974 | A1 | 1/2007 | Higgins |
| 2007/0050215 | A1 | 3/2007 | Kil |
| 2008/0109252 | A1 | 5/2008 | LaFountain |

(Continued)

OTHER PUBLICATIONS

Lara Allet, et al., Wearable systems for monitoring mobility-related activities in chronic disease: A systematic review. Sensors. Sep. 2010, pp. 9026-9052.

(Continued)

*Primary Examiner* — Gregory D. Moseley
(74) *Attorney, Agent, or Firm* — Joseph Petrokaitis; Otterstedt, Wallace & Kammer, LLP

(57) ABSTRACT

A method includes loading a software application onto a data capture device of a subject, collecting electronic texts of a subject from a plurality of computer storage devices across the Internet, including electronic text generated by the data capture device, identifying, from the electronic texts, one or more perceptions held by the subject, generating a classification for each of the perceptions, wherein at least one of the perceptions is classified as a negative perception, defining an engagement degree of the subject with a current engagement model using the classifications of the perceptions, analyzing the negative perception, and defining a score for each of a plurality of strategies of engagement, wherein at least one strategy is selected, using the scores, for application to the subject, and the application of a selected strategy includes transmitting configuration data to the data capture device of the subject, the configuration data updates the software application.

12 Claims, 9 Drawing Sheets

400
start
404 Analysis patient's perceptions
405 Classify the perceptions
406 Define the engagement degree
403 Engagement Data
402 Patient Data
401 Text authored from a patient
407 Analysis negative perceptions
408 Define the score of the strategies
409 Present engagement degree and score of strategies
End

(56) References Cited

U.S. PATENT DOCUMENTS

2011/0078167 A1* 3/2011 Sundaresan ......... G06F 17/2785 707/765
2011/0106556 A1 5/2011 Patel
2012/0154582 A1 6/2012 Johnson
2013/0226617 A1 8/2013 Mok
2013/0282430 A1* 10/2013 Kannan .................. G06Q 30/06 705/7.29
2013/0326375 A1* 12/2013 Barak ................... H04L 65/403 715/758
2014/0039804 A1* 2/2014 Park ..................... A61B 5/0002 702/19
2014/0358581 A1* 12/2014 Sudharsan ............. G06N 7/005 705/2
2014/0365240 A1* 12/2014 Canton .............. G06Q 30/0201 705/3
2015/0088536 A1* 3/2015 Thelen ................... G16H 40/67 705/2
2015/0150023 A1* 5/2015 Johnson ................ G06F 9/5027 718/107
2015/0216413 A1* 8/2015 Soyao .................. A61B 5/0022 709/204
2015/0324360 A1* 11/2015 Dakshinamurthy ......................... G06F 17/30864 707/728
2015/0356701 A1* 12/2015 Gandy ................... G06Q 10/10 705/2

OTHER PUBLICATIONS

Michel Klein, Intelligent Mobile Support for Therapy Adherence and Behavior Change, J Biomed Inform. Oct. 2014, pp. 141-157.

* cited by examiner

MEASUREMENT, ANALYSIS AND APPLICATION OF PATIENT ENGAGEMENT

BACKGROUND

The present disclosure relates to automatic text classification in a patient engagement application.

According to the World Health Organization (WHO), patient engagement is ignored in many cases (e.g., ignored by most countries and healthcare institutions). Evidence suggests that patients who are engaged tend to require fewer health care treatments, make better decisions and have better health outcomes.

BRIEF SUMMARY

According to an exemplary embodiment of the present invention, a method includes loading a software application onto a data capture device of a subject, wherein the data capture device generates at least one electronic text, collecting electronic texts of a subject from a plurality of computer storage devices across the Internet, including the at least one electronic text generated by the data capture device, identifying, from the electronic texts, one or more perceptions held by the subject, generating a classification for each of the one or more perceptions, wherein at least one of the perceptions is classified as a negative perception, defining an engagement degree of the subject with a current engagement model using the classifications of the one or more perceptions, analyzing the negative perception, and defining a score for each of a plurality of strategies of engagement, wherein at least one strategy is selected, using the scores, for application to the subject, and the application of a selected strategy includes transmitting configuration data to the data capture device of the subject, the configuration data updates the software application As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. For example, one or more embodiments may provide one or more of the following advantages:

address the issue of patient engagement,
select effective patient-engagement strategies,
lower healthcare resource use; and
achieve improved healthcare results.

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Figure 1:
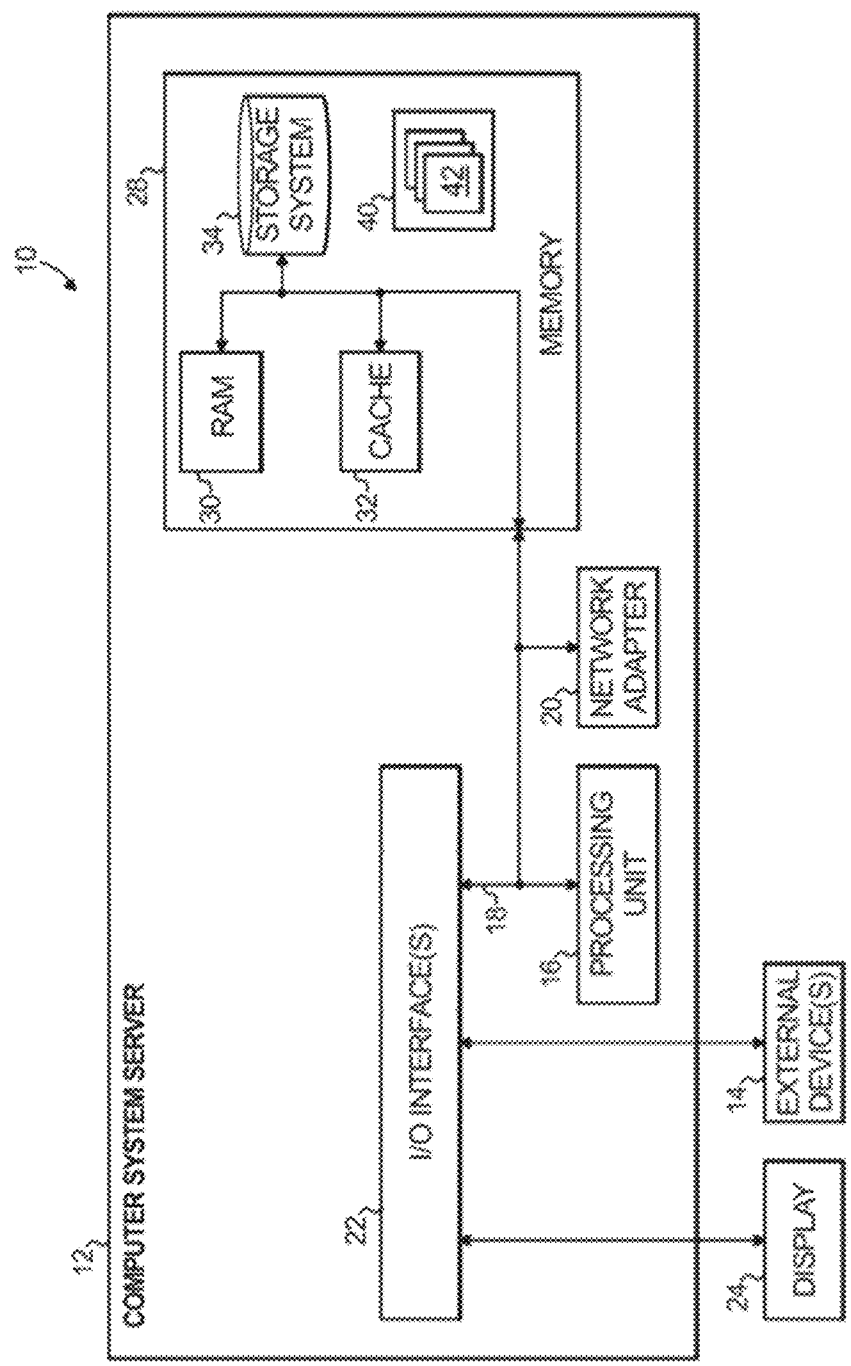
FIG. 1 depicts a cloud computing node according to an embodiment of the present invention.

Strategies for improving patient engagement have been recommended by the WHO for improving different aspects of patient engagement. Different strategies are configured to improve patients' health literacy, treatment decision-making, self-management of chronic conditions, etc. Embodiments of the present invention include methods and systems enabling stakeholders (e.g., governments, health authorities or payers) to leverage electronic communications to select one or more strategies likely to improve a patient's treatment and to communicate information to the patient designed to increase patient engagement. Embodiments of the present invention include specific improvements of applications running on a computer.

In one or more embodiments of the present invention, a computer system evaluates text generated about and/or by a patient. This text can be sourced from electronic heath records (EHRs), electronic medical records (EMRs), and the like. One or more of the embodiments can be facilitated by, for example, wearable sensors, ingestible sensors, Medication Event Monitoring Systems (MEMS) and mobile applications. According to an embodiment of the present invention, a software application is loaded onto a data capture device of a subject, wherein the data capture device generates at least one electronic text. These approaches can automatically collect data from patients in their daily livings, monitor objective and subjective variables and help to identify adherence behavior and generate text (patient data) that can be processed. Data generated by these devices is stored in a patient data memory device for later processing, e.g., analysis of negative perceptions.

According to an exemplary embodiment of the present invention, automatic text classification and sentiment analysis techniques are applied to patient authored texts. The method assesses available patient engagement and intervention strategies and applies one or more of these strategies to improve patient engagement. Automatic text classification is applied to the patient texts to classify a previously chosen model of patient engagement. Sentiment analysis is applied to the patient texts to determine positive or negative aspects of the texts according to an engagement contribution. A quantitative assessment is output as a patient engagement degree, calculated using weights on perceptions and a count of positive or negative aspects of the patient texts. According to an exemplary embodiment of the present invention, the qualitative assessment is a top-n ranking of negative aspects. In at least one embodiment, sentiment analysis is used for negative aspects of the patient texts, connecting the negative aspects into all available intervention strategies. According to an exemplary embodiment of the present invention, additional information, such as patient data (e.g., diagnosis, age, gender, current health state, etc.), is used to calculate a score of each intervention strategy applicable to the patient. The additional information can be generated by one or more sensors, MEMS, EMRs, EHRs, Personal Health Records (PHRs), etc.

Definitions:

Patient Compliance: the degree to which a patient adheres to a prescribed medical treatment.

Patient Adherence: refers to the continuity of the medical treatment and it depends on a number of factors that determines it (cost of the medication, complexity of the treatment, etc.).

Patient engagement: refers a patient that takes an active role as a key player in protecting his health, choosing appropriate treatments for episodes of ill health and managing chronic disease.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Figure 2:
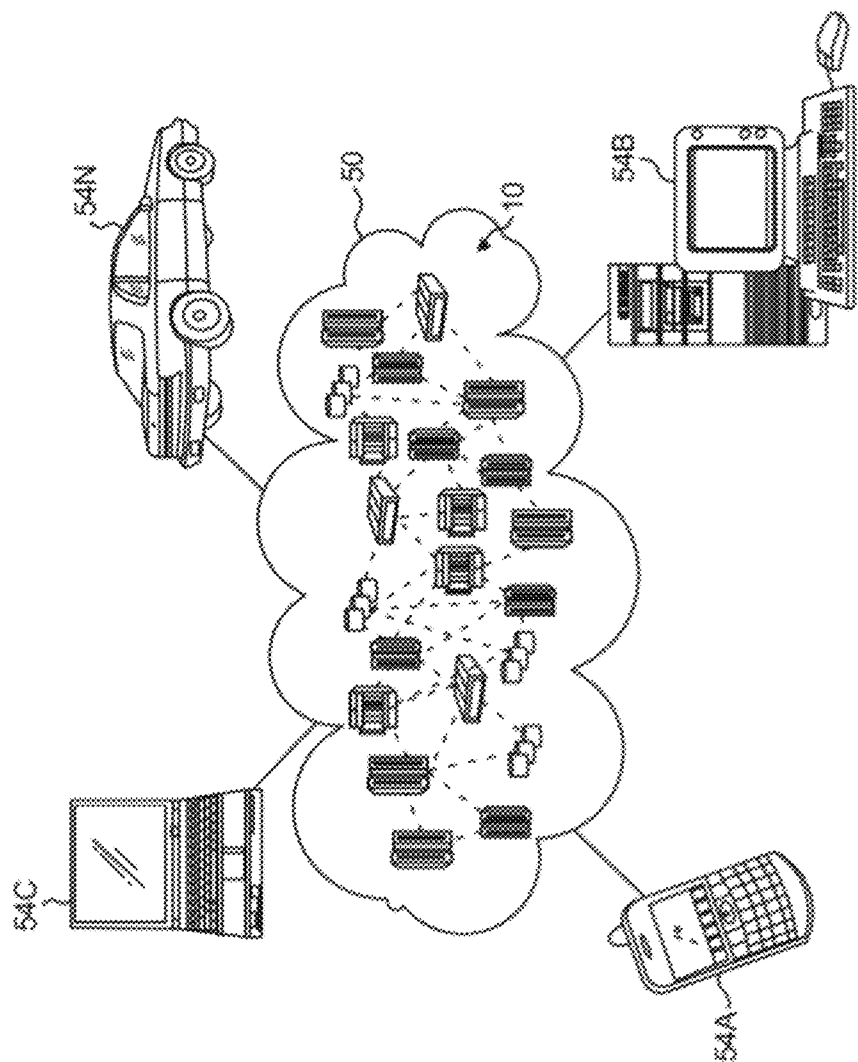
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
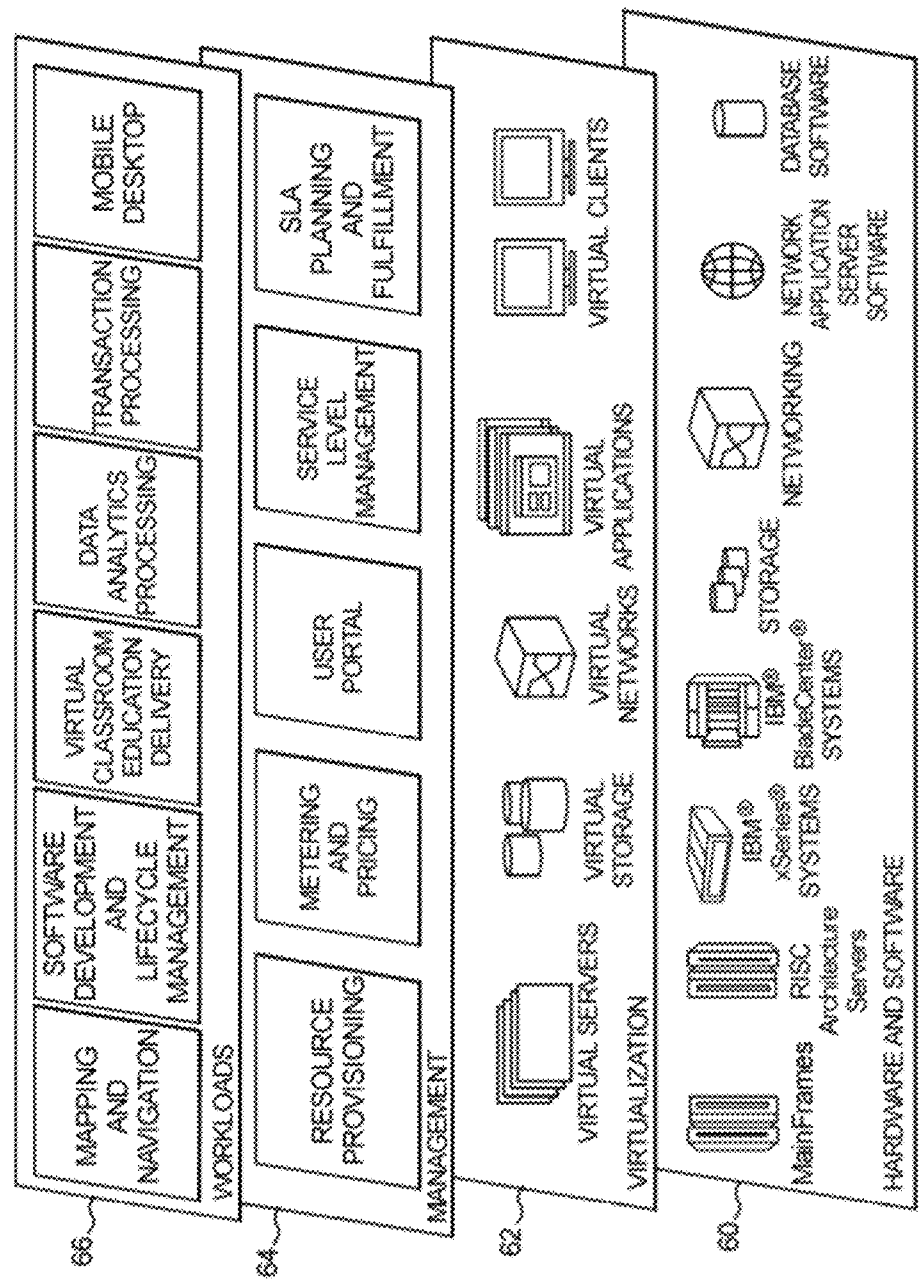
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM Web Sphere® application server software; and database software, in one example IBM DB2® database software. (IBM, zSeries, pSeries, xSeries, BladeCenter, Web Sphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and mobile desktop.

Figure 4:
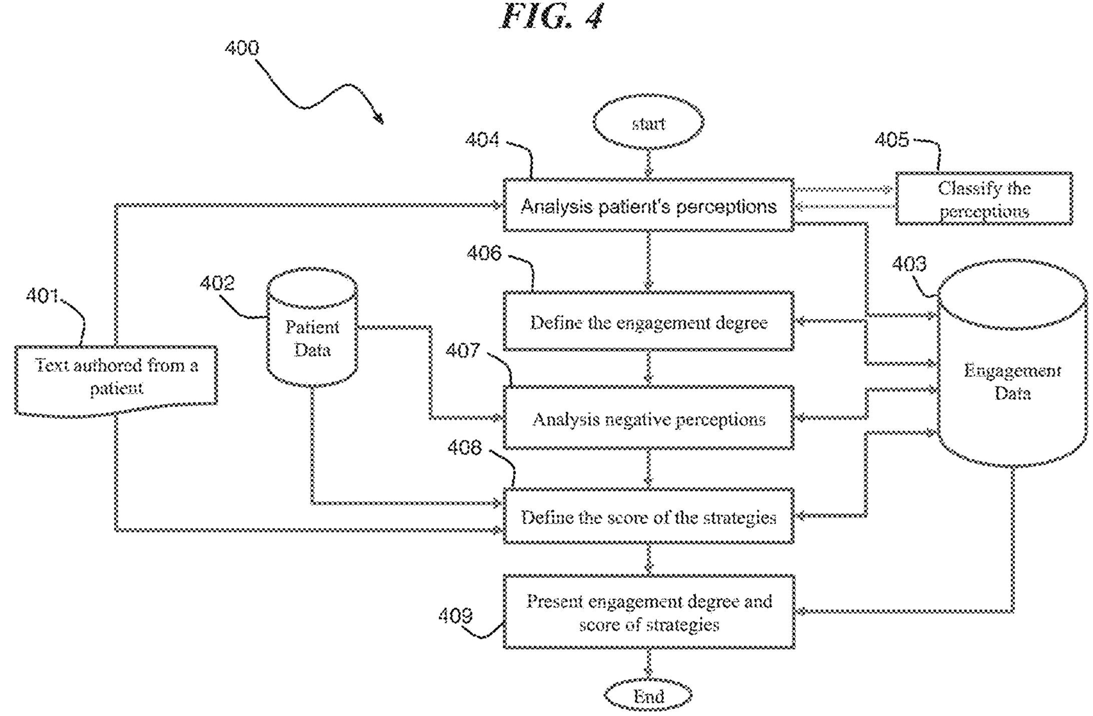
FIG. 4 is a flow diagram of a method according to an embodiment of the present invention.

Referring to FIG. 4, according to an embodiment of the present invention, a system 400 uses texted authored by a patient 401, patient data 402 and engagement data 403 as input. The patient authored texts 401 include texts that contain relevant information describing patient's opinions, sentiments and points of view related to health topics related with his diseases. These texts are collected from electronic sources including a data capture device, social media (e.g., TWITTER, FACEBOOK, etc.), healthcare social media (PATIENTSLIKEME, etc.), doctor-patient conversations captured in email or obtained texts of interviews recording, patient surveys, patient portals, patient interviews, etc. In at least the case of the data capture device, a software application is loaded onto the data capture device of patient, wherein the data capture device generates at least one electronic text. The patient data 402 includes patient structured data from EMR, EHR or hospital information systems (HIS). The engagement data 403 is a database storing data related with the engagement things of each analyzed patient.

It should be understood that the patient authored texts 401, patient data 402 and engagement data 403 are embodied by memory devices, including computer servers, computer databases, the data capture device, and the like. At module 404, patient's perceptions of a current healthcare strategy are analyzed. At module 404, the patient texts are retrieved and analyzed. Module 404 uses a classification module 405 (see also FIG. 5) to classify fragments of authored texts in terms of perceptions and polarity (i.e., positive or negative). With this information, a weight for each perception is defined. The date of the analysis, patient identification, fragments of the patient texts, the classification perception of the fragments and the polarity of the fragments and weight of each perception is stored in the engagement data 403. At module 405, the perceptions are classified. Module 405 classifies fragment of the patient texts into one or more of the perceptions of a current patient engagement model or health behavior change model (e.g., transtheoretical model, health belief model, theory of planned behavior, etc.). The module 405 defines the polarity of the fragment as a positive or negative engagement contribution. At module 406, the engagement degree is defined. Module 406 obtains the patient's data from the engagement data database 403 and calculates the patient engagement degree (e.g., on a scale of 0 to 100 percent). At module 407, negative perceptions are analyzed. Module 407 obtains the patient's fragments of authored text that are classified as a negative perception from the engagement data 403 and assigns to each one all the related strategies (e.g., health literacy, shared decision-making and/or self-management). Module 407 obtains, from the patient data 402, data used to review the available strategies associated with the fragment. Module 407 reclassifies the fragment using the engagement degree. Module 407 stores the connection to one or more related strategies in the engagement data database 403. In this way the patient data can be used to improve the understanding of the fragment. At module 408, the score of the strategies is defined. Module 407 obtains the patient's data from the engagement data database 403 and patient data 402 to calculate the score of each strategy assigned to the patient. Module 407 stores the result into the engagement data database 403. At module 409, the top-n negative perceptions are ranked and presented (e.g., displayed, communicated to a caregiver's computer, etc.) as a result of the patient engagement degree, a score of the strategies and a qualitative list of the top-n negative perceptions with the list of the strategies associated to the perception.

In at least one embodiment, at module 409, at least one strategy is selected, using the scores, for application to the patient, and the application of a selected strategy by module 409 includes transmitting configuration data via the Internet to the data capture device of the patient, the configuration data updating the software application, for example, to relay health literacy information likely to increase patient engagement, to coach the patient to use shared decision-making, and improved self-management (e.g., such as by reminders to perform certain tasks). According to at least one embodiment of the present invention, transmitting the configuration data to the data capture device of the subject comprises transmitting the configuration data directly to the data capture device (see for example, computer system 1200, FIG. 12) via a wireless connection (see for example, Network OF 1205, FIG. 12). According to at least one embodiment of the present invention, transmitting the configuration data to the data capture device of the subject comprises transmitting the configuration data to a computer, wherein the configuration data updates the software application of the data capture device during a subsequent update facilitated by the computer.

Figure 5:
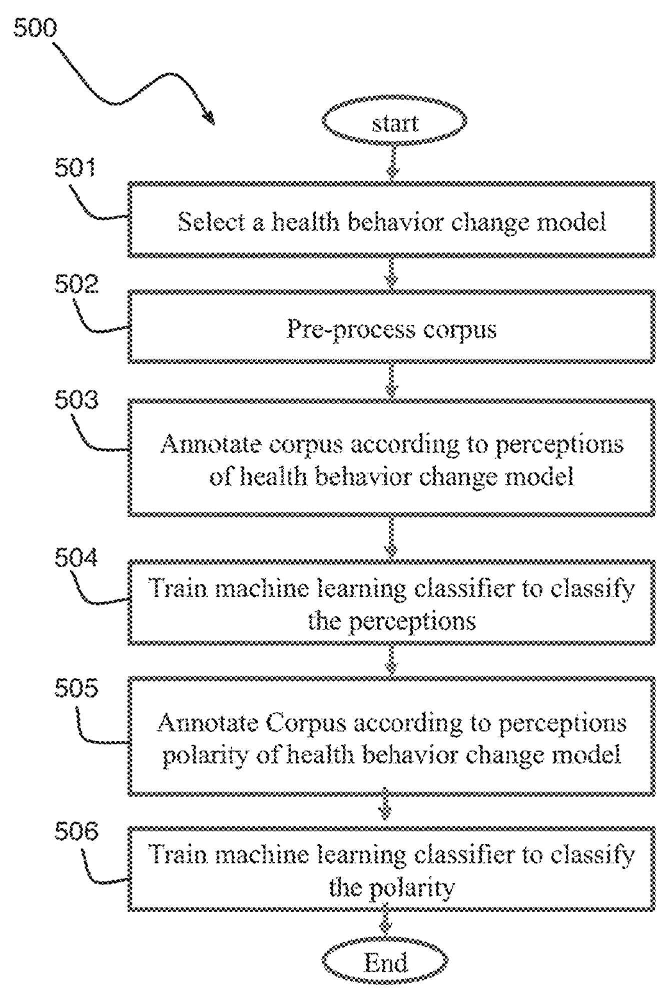
FIG. 5 is a flow diagram of a method for building a classify perception module according to an embodiment of the present invention.

FIG. 5 is a flow diagram of a method 50 for building a classify perception module 405 according to an embodiment of the present invention. The classify module 405 classifies fragments of authored texts (see FIG. 6). The method 500 includes selecting a health behavior change model 501, wherein the health behavior change model provides a foundation for the patient adherence assessment. Models of health behavior change have in common the perceptions, which are the patient's points of view related to medical staff and infrastructure, disease, treatment and of the patient (self). At 502, the method 500 preprocesses a corpus of the patient texts. Existing text pre-processing techniques can be used for cleaning and preparation of data for later classification. At 503, the method annotates the corpus according to perceptions (e.g., by severity, vulnerability, benefits, etc.) of a health behavior change model. Optionally, a manual annotation can be performed by a human expert to classify fragments of patient authored text according to perceptions of a previously selected health behavior change model. At 504, the method 500 includes training a machine learning classifier to classify the perceptions. An automatic text classifier is trained using the corpus that was processed and annotated. At 505, the corpus is annotated according to patient perceptions, polarity (e.g., as positive or negative) of fragments, and a current health behavior change model. Optionally, a manual annotation can be performed by human experts to classify fragments of patient authored text according as positive or negative indications of an adherence contribution to the current health behavior change model. At 506, the method 500 includes training a machine learning classifier (see module 405, FIG. 4) to classify the polarity of the fragments. The automatic text classifier is trained using the corpus that was processed and annotated.

It should be understood that the training modules 504 and 506 can use various machine learning methods, such as naïve Bayes, support vector machines (SVM), multilayer perceptron (MLP) and the like.

Figure 6:
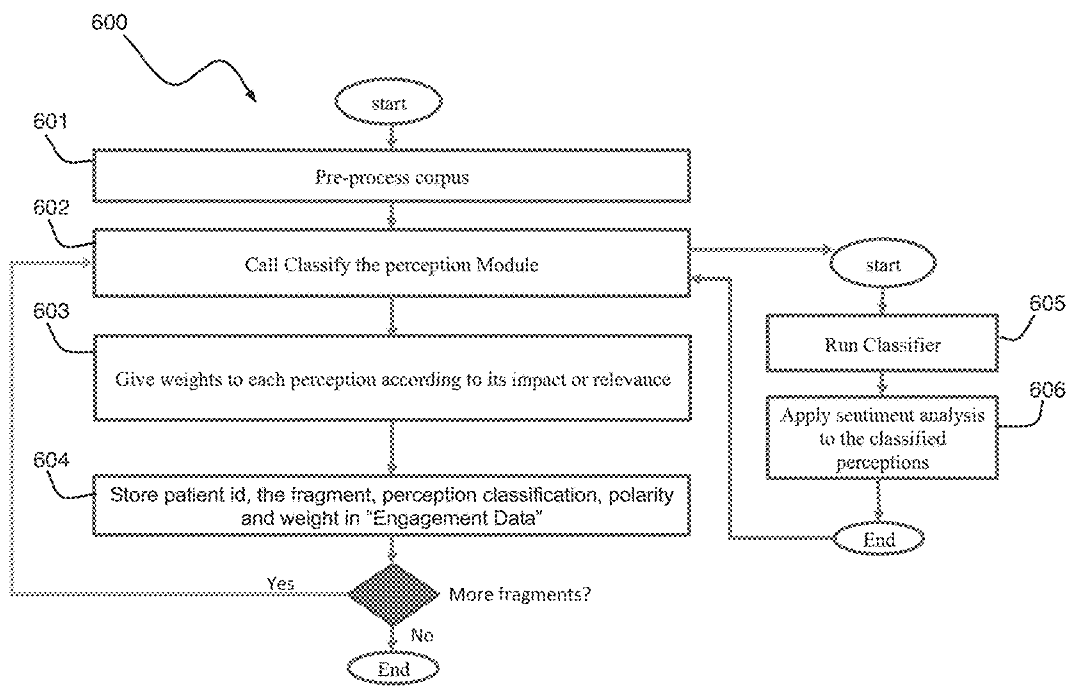
FIG. 6 is a flow diagram of a method for classifying fragments in perceptions according to an embodiment of the present invention.

FIG. 6 is a flow diagram of a method 600 for classifying fragments in perceptions according to an embodiment of the present invention. As shown in FIG. 6, the classifier 401 is executed 605 on the authored text from a patient. The classifier 401 classifies the text fragments in the perceptions of the previously chosen model of behavior change. At 606, the method 600 applies a sentiment analysis to the classified perceptions. The output includes perceptions classified as positive or negative to engagement contribution (e.g., a positive perception indicates an increase in patient engagement and a negative perception indicates a decrease in patient engagement). The sentiment analysis can use machine learning, neuro-linguistic programming (NLP), sentiment dictionary, etc.

Referring to FIG. 6, at 601 the patient authored text is pre-processed (e.g., sentence split, stop work removal, stemming, etc.). Existing text pre-processing techniques can be used for the cleaning and preparation of data for the classifier. At 603, the method 600 includes calling the classifier 405 to obtain the classifier 405. This is also shown at 605-606. The result will be the perception classification and the polarity of the fragment. At 603, the method 600 includes weighting each perception according to its impact or relevance. Each perception of the previously chosen model of behavior change can have a different impact or relevance to patient engagement. According to at least one embodiment of the present invention, a weight is assigned to each perception to adjust this relevance. High weights indicate that the perception has a high positive or negative significance to patient engagement, while low weights indicate that the perception has a high positive or negative significance to patient engagement. At 604, the method 600 includes storing patient identification, the fragment, perception classification, polarity and weight in the engagement data database 403 as a tuple or row. Each tuple contains the patient identification, fragment, perception name, weight and the polarity as positive or negative.

Figure 7:
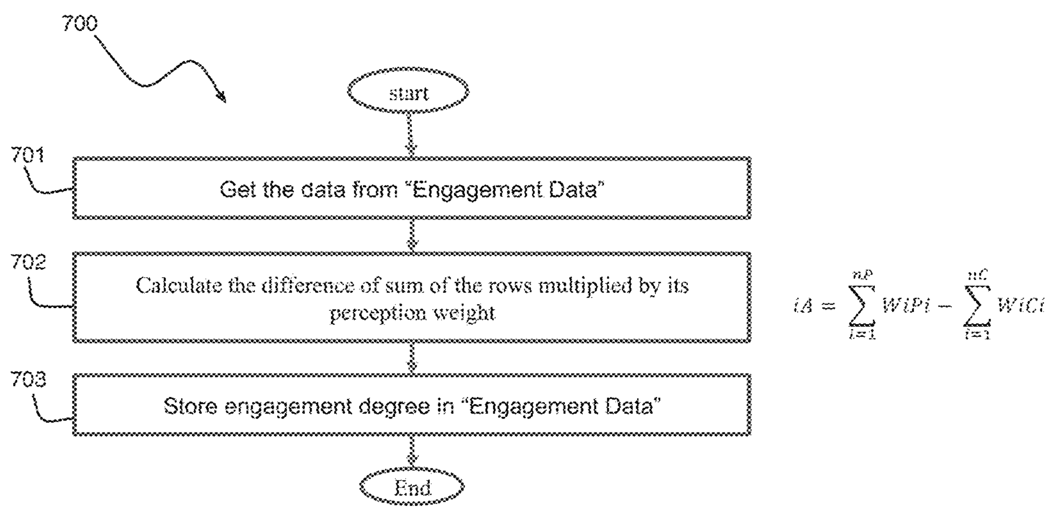
FIG. 7 is a flow diagram of a method for analyzing a fragment of authored text according to an embodiment of the present invention.

FIG. 7 is a flow diagram of a method 700 for analyzing a fragment of authored text according to an embodiment of the present invention. Referring to FIG. 7, the method 700 includes defining an engagement degree module. This module calculates the patient engagement degree. More particularly, at 701, the method 700 includes obtaining the data from engagement data database 403 to obtain a perception name, its polarity and weight. At 702, the method 700 includes calculating a difference of the sums of the tuples (or rows) multiplied by corresponding perception weights (Wi). For each polarity in the table filled with the data classified and polarized (Pi—positive perception and Ci—negative perception), multiply the perception weight by the perception frequency (nP—number of positives and nC—number of negatives). The difference between positive and negative values is then calculated (iA—engagement score). Positive values means the patient has more positive adherence perceptions, according to the previously chosen model of behavior change. The higher this value, the more likely it is that the patient is following the medical recommendations. Negative values means the patient has more negative adherence perceptions, according to the previously chosen model of behavior change. The lower this value, the more likely is the patient to be following the medical recommendations. At 703, the method includes storing the engagement degree in the engagement data 403.

Figure 8:
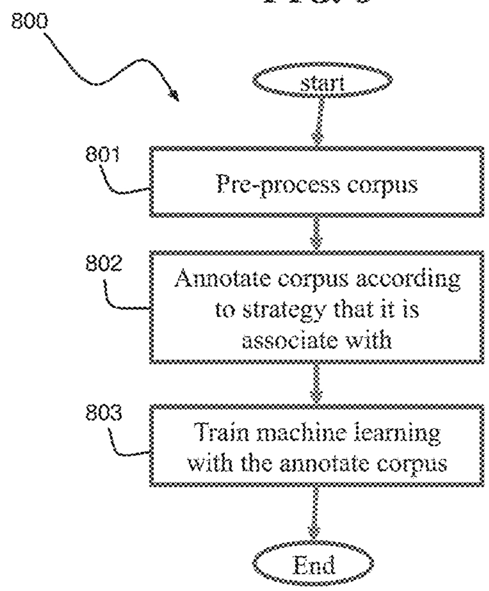
FIG. 8 is a flow diagram of a method for calculating patient engagement degree according to an embodiment of the present invention.

FIG. 8 is a flow diagram of a method 800 for calculating patient engagement degree according to an embodiment of the present invention. Referring to FIG. 8, a method 800 of analyzing negative perceptions is performed. The method 800 enables the strategies to be associated with the fragment of the authored text. At 801, the method 800 includes a pre-processing of the corpus. Existing text pre-processing techniques can be used for the cleaning and preparation of data for the associator 802. At 802, the method 800 includes annotating the corpus according to a strategy that is associated with. In this step, fragments are classified. For example, a fragment can be classified as being indicative of a health literacy problem if it is determined that a fragment indicates that the patient didn't understand how to use certain medication. In another example, in a case where the patient text reveals that the patient arrived at a decision without consultation, a corresponding fragment can be classified as being indicative of a lack of shared decision making. In yet another example, in a case where the patient text reveals a lack of understanding about how and/or why to use certain medication, then a corresponding fragment can be classified as indicative of self-management orientation. Self-management orientation includes the actions that people take to recognize, treat and manage their own health problems, independently of the medical system. Optionally, at 802 a manual annotation can be performed by a human expert to classify fragments of patient authored text according to a strategy. The strategy can be one recommended by WHO (e.g., health literacy, shared decision-making and self-management). At 803, the method 800 includes training machine learning with the annotate corpus. More particularly, an automatic strategy association is trained to the fragment authored text using the corpus that was processed and annotated.

Figure 9:
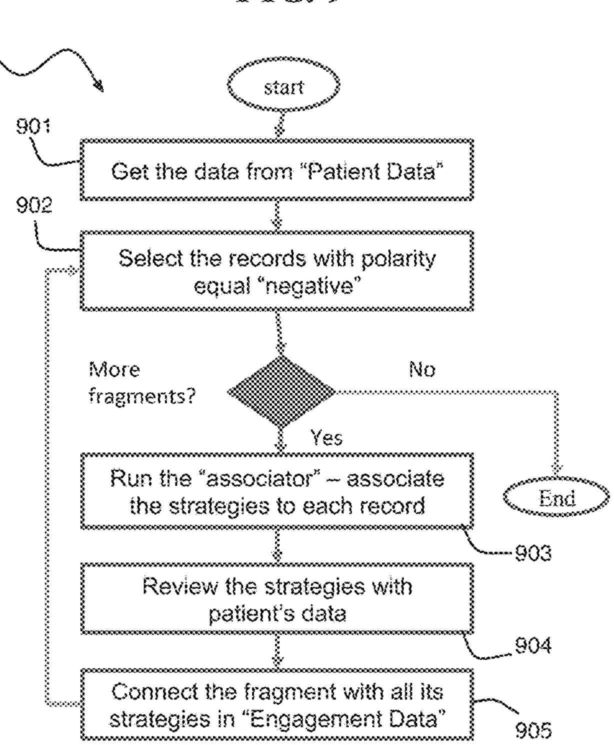
FIG. 9 is a flow diagram of a method for building a mechanism that can associate strategies to authored text according to an embodiment of the present invention.

FIG. 9 is a flow diagram of a method 900 for building a mechanism that can associate strategies to authored text according to an embodiment of the present invention. Referring to FIG. 9, a method 900 includes obtaining a particular patient's records from the patient data 402 and using the patient's data to select one or more strategies designed to address particular patient engagement recommendations 901. The particular patient's records can be used to refine a classification of a fragment associated with the patient. For example, for a young patient (i.e., less than 2 years old), certain health literacy strategies can be ruled out, and the system can operate efficiently by searching for alternative strategies to implement, i.e., other than health literacy strategies. The patient records can include data for the patient's age, gender, level of educational attainment, diagnostics, current health state, Nursing Interventions Classification (NIC)/Nursing Outcomes Classification (NOC)/North American Nursing Diagnosis Association (NANDA) diagnostics, socioeconomic status, etc. At 902, the method 900 includes selecting the records with polarity equal to "negative." From the engagement data database 403, select the records that are classified as a negative perception to the engagement patient degree. At 903, the method 900 includes executing the associator 802 to obtain a patient's fragment authored text. The associator 802 associates the text fragments in all strategies that are related with the text. At 904, the method 900 includes a review of the strategies with patient's data 402. The patient data is used to review the association. If any strategy isn't associated correctly, it is changed it to the right one. For example: if the patient has a lower education level, the module analyzes the written texts in order to review the health literacy problem. At 905, the method 900 includes connecting the fragment with all its strategies in the engagement data database 403. The connection of each strategy to the fragment text is stored in the engagement data database 403.

Figure 10:
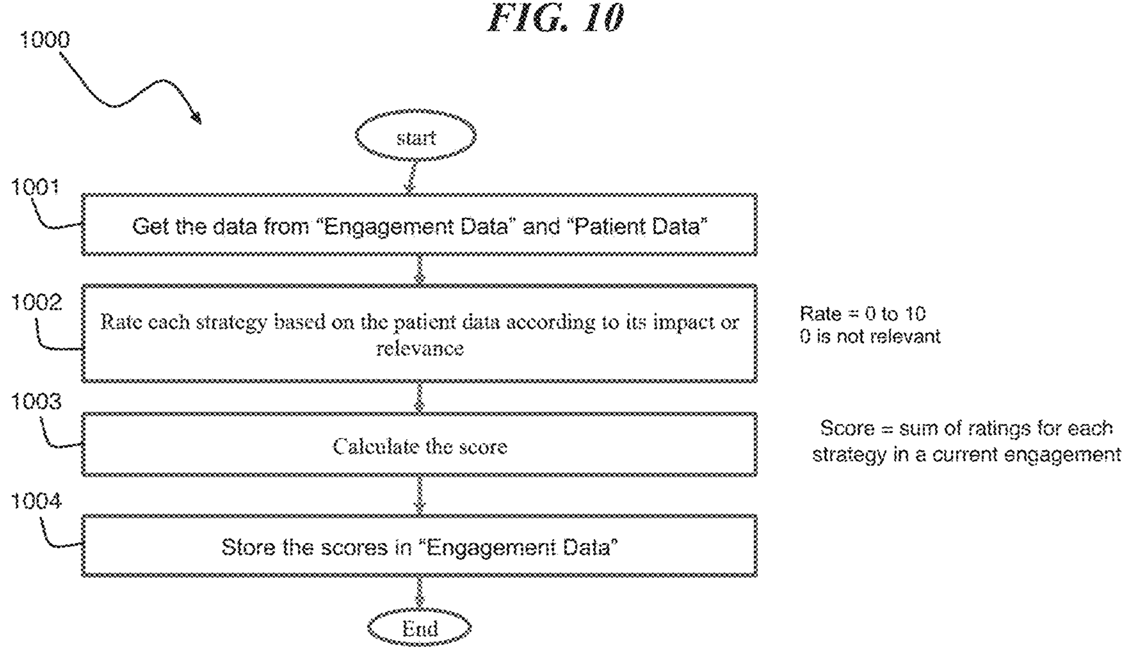
FIG. 10 is a flow diagram of a method for analyzing negative perceptions according to an embodiment of the present invention.

FIG. 10 is a flow diagram of a method 1000 for analyzing negative perceptions according to an embodiment of the present invention. Referring to FIG. 10, the method 1000 performed by a strategies module for defining a score of the strategies for the patient engagement recommendations. The strategies module calculates the score of the strategies for the patient engagement recommendations. At 1001, the method 1000 obtains the data from engagement data database 403 and patient data 402. The quantity of each strategy in the engagement data database 403 is summed. The method obtains data from the patient data 402 that can associate the strategy to address the patient engagement recommends by WHO. For example: age, gender, education, diagnostics, current health state, NIC/NOC/NANDA diagnostic, socioeconomic status, etc. At 1002, the method 1000 includes rating each strategy based on the patient data according to its impact or relevance. For each patient, the data in the engagement database should have a different impact or relevance to patient engagement strategy. A possible adjustment to the engagement strategy assessment includes rating each concept within the patient information that is known about the patient. The value of the rating is given in a range from 0 to 10, in which 0 is not relevant/no impact. At 1003, the method 1000 includes calculating the score for a current patient engagement, wherein the score is a sum of ratings for individual strategies (e.g., different strategies designed to improve health literacy, shared decision-making and/or self-management) used in a current patient engagement model. For example: Patient X has 10 health literacy recommendations and the patient is 65 years and has a lower educational attainment, where the expert rating condition is 10, so the final score to this patient will be 20. At 1004, the method 1000 includes storing the scores of each strategy in engagement data database 403. According to an embodiment of the present invention, strategies with higher scores have a higher priority to be implemented in a subsequent (e.g., updated) patient engagement model, wherein a patient engagement model is selected according to the scores.

Figure 11:
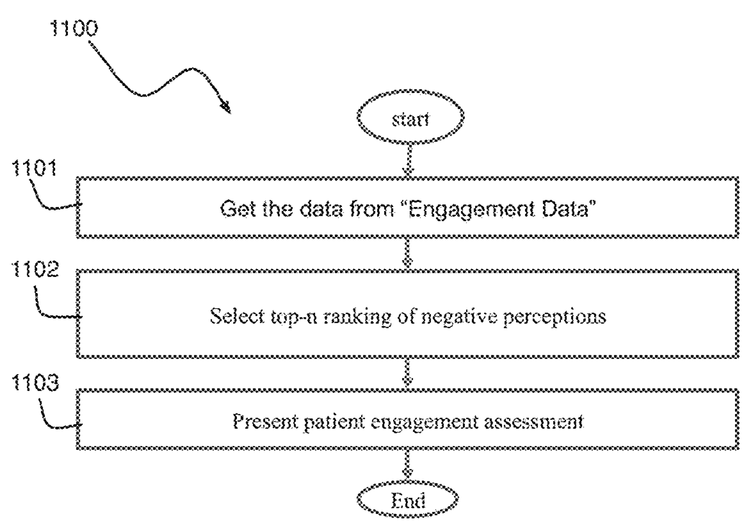
FIG. 11 is a flow diagram of a method for calculating a score of strategies according to an embodiment of the present invention.

FIG. 11 is a flow diagram of a method 1100 for calculating a score of strategies according to an embodiment of the present invention. Referring to FIG. 11, a present engagement degree and score of strategies module presents the result of analysis of the patient engagement. At 1101, the method 1100 includes obtaining the data from engagement data database 403, which can include patient-id, fragment, perception name, weight, polarity, patient engagement degree, health literacy score, shared decision-making score and self-management score. At 1102, the method 1100 includes selecting the top-n ranking of negative perceptions. From the table, select the top-n row according to the multiplication of the perception weight by the perception frequency. These rows are the most negative perceptions with the higher impact or relevance according to the given weights. These negative perceptions are likely the main factor for low adherence, and represent the best potential for medical interventions aims. At 1103, the method 1100 includes presenting a patient adherence assessment. The patient adherence assessment includes the patient engagement degree, the qualitative list of the top-n negative perceptions with the list of the strategies associated to the perception and the strategies scores order by the higher value to the lower value.

Use Cases:

1. A doctor wants to know if a patient is engaged or satisfied with the current treatment. The doctor uses the system to calculate the engagement degree of the patient and determine the score of a shared decision-making. Also, the system can be used to determine if another strategy can be implemented with the patient.

2. A care coordinator uses the system to calculate the engagement degree of a set of patients and also to determine which patients require interventions according to the score of the strategies. Depending on the strategies, the care coordinator knows that the care team or the patients require additional guidance.

3. A healthcare provider can use the system to determine the engagement degree to better classify their clients and use this to promote different pricing strategies. They can also promote health with costly patients, plan a patient-engagement program tailored to their clients and share resources based on one or more selected strategies and the engagement degree.

Recapitulation:

According to an embodiment of the present invention, a method includes loading a software application onto a data capture device of a subject, wherein the data capture device generates at least one electronic text, collecting electronic texts of a subject from a plurality of computer storage devices across the Internet, including the at least one electronic text generated by the data capture device, identifying, from the electronic texts, one or more perceptions held by the subject, generating a classification for each of the one or more perceptions, wherein at least one of the perceptions is classified as a negative perception, defining an engagement degree of the subject with a current engagement model using the classifications of the one or more perceptions, analyzing the negative perception, and defining a score for each of a plurality of strategies of engagement, wherein at least one strategy is selected, using the scores, for application to the subject, and the application of a selected strategy includes transmitting configuration data to the data capture device of the subject, the configuration data updates the software application.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a “processor,” “circuit,” “module” or “system.”

Furthermore, it should be noted that any of the methods described herein can include an additional step of providing a computer system for automatic text classification in a patient engagement application. Further, a computer program product can include a tangible computer-readable recordable storage medium with code adapted to be executed to carry out one or more method steps described herein, including the provision of the system with the distinct software modules.

Figure 12:
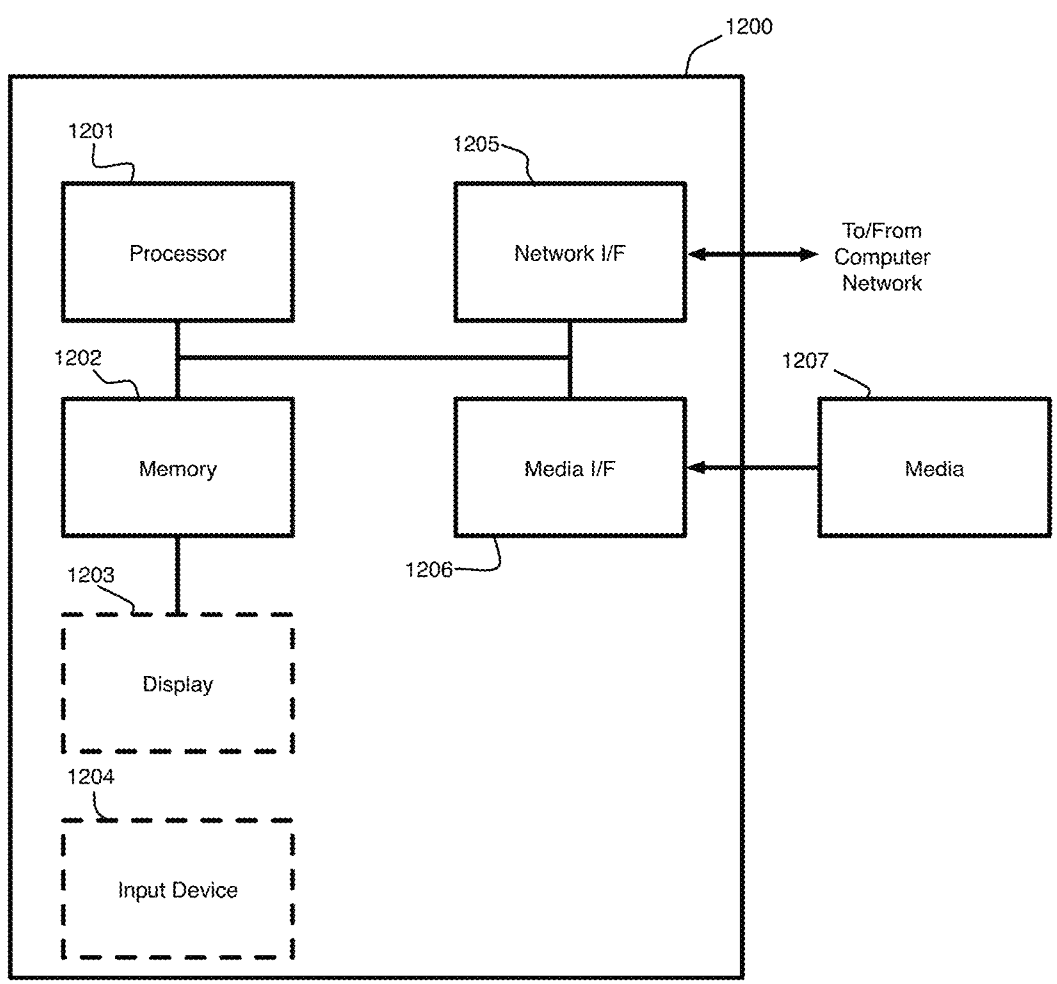
FIG. 12 is a block diagram depicting an exemplary computer system embodying a method automatic text classification in a patient engagement application according to an exemplary embodiment of the present invention.

Referring to FIG. 12; FIG. 12 is a block diagram depicting an exemplary computer system 1200 embodying the computer system for automatic text classification in a patient engagement application (see FIG. 4) according to an embodiment of the present invention. The computer system shown in FIG. 12 includes a processor 1201, memory 1202, display 1203, input device 1204 (e.g., keyboard), a network interface (I/F) 1205, a media I/F 1206, and media 1207, such as a signal source, e.g., camera, Hard Drive (HD), external memory device, etc.

In different applications, some of the components shown in FIG. 12 can be omitted. The whole system shown in FIG. 12 is controlled by computer readable instructions, which are generally stored in the media 1207. The software can be downloaded from a network (not shown in the figures), stored in the media 1207. Alternatively, software downloaded from a network can be loaded into the memory 1202 and executed by the processor 1201 so as to complete the function determined by the software.

The processor 1201 may be configured to perform one or more methodologies described in the present disclosure, illustrative embodiments of which are shown in the above figures and described herein. Embodiments of the present invention can be implemented as a routine that is stored in memory 1202 and executed by the processor 1201 to process the signal from the media 1207. As such, the computer system is a general-purpose computer system that becomes a specific purpose computer system when executing routines of the present disclosure.

Although the computer system described in FIG. 12 can support methods according to the present disclosure, this system is only one example of a computer system. Those skilled of the art should understand that other computer system designs can be used to implement embodiments of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:

loading a software application onto a data capture device of a subject, wherein the data capture device generates at least one electronic text;

collecting electronic texts of the subject from a plurality of computer storage devices across a computer network, including the at least one electronic text generated by the data capture device;

identifying a plurality of fragments of the electronic texts;

identifying a perception of the subject from each of two or more of the fragments;

generating a classification for each of the perceptions as being related to one or more of a plurality of strategies of engagement, including a first strategy currently assigned to the subject;

determining a polarity of each of the perceptions, wherein a polarity of at least one of the perceptions is a negative polarity and a polarity of at least another one of the perceptions a positive perception;

determining a weight of each of the perceptions, wherein weight indicates a relevance of the perception;

defining an engagement degree of the subject with the first strategy using the classifications, polarities, and weights of the perceptions, and a frequency of each of the perceptions identified in the fragments of the electronic texts;

calculating a score for each of a plurality of strategies of engagement classified as being related to the at least one negative perception, including the first strategy and a second strategy, wherein the second strategy is not currently assigned to the subject; and selecting the second strategy for assignment to the subject from among the plurality of strategies based on the scores for the strategies of engagement classified as being related to with the at least one negative perception, and the application of the second strategy includes transmitting configuration data to the data capture device of the subject, wherein the configuration data updates the software application to implement the second strategy.

2. The method of claim 1, wherein transmitting the configuration data to the data capture device of the subject comprises transmitting the configuration data directly to the data capture device via a wireless connection.

3. The method of claim 1, wherein transmitting the configuration data to the data capture device of the subject comprises transmitting the configuration data to a computer, wherein the configuration data updates the software application of the data capture device during a subsequent update facilitated by the computer.

4. The method of claim 1, wherein defining the engagement degree of the subject comprises:

calculating, for each of the fragments having an identified perception, a product of the weight of the identified perception and the frequency of the perception identified in the fragments; and calculating the engagement degree as a sum of the products for all of the fragments having identified perceptions.

5. The method of claim 1, wherein generating the classification for each of the perceptions further comprises annotating a corpus comprising the electronic texts.

6. The method of claim 1, wherein a plurality of the perceptions are classified as a negative perception, wherein calculating the score for each of the plurality of strategies of engagement classified as being related to the at least one negative perception further comprises:

ranking each of the negative perceptions according to a multiplication of the respective perception weight by the respective perception frequency; and calculating the score for each of a plurality of strategies of engagement classified as being related to the at least one negative perception, according to a sum of the rankings.

7. A computer program product for configuring a data capture device, the computer program product comprising a computer readable storage medium having program instructions embodied therewith, the program instructions executable by a processor to cause the processor to:

load a software application onto the data capture device of a subject, wherein the data capture device generates at least one electronic text;

collect electronic texts of the subject from a plurality of computer storage devices across a computer network, including the at least one electronic text generated by the data capture device;

identify a plurality of fragments of the electronic texts;

identify a perception of the subject from each of two or more of the fragments;

generate a classification for each of the perceptions as being related to one or more of a plurality of strategies of engagement, including a first strategy currently assigned to the subject;

determine a polarity of each of the perceptions, wherein a polarity of at least one of the perceptions is a negative polarity and a polarity of at least another one of the perceptions a positive perception;

determine a weight of each of the perceptions, wherein weight indicates a relevance of the perception;

define an engagement degree of the subject with the first strategy using the classifications, polarities, and weights of the perceptions, and a frequency of each of the perceptions identified in the fragments of the electronic texts;

calculate a score for each of a plurality of strategies of engagement classified as being related to the at least one negative perception, including the first strategy and a second strategy; and select the second strategy for assignment to the subject from among the plurality of strategies based on the scores for the strategies of engagement classified as being related to with the at least one negative perception, and the application of the second strategy includes transmitting configuration data to the data capture device of the subject, wherein the configuration data updates the software application to implement the second strategy.

8. The computer program product of claim 7, wherein transmitting the configuration data to the data capture device of the subject comprises transmitting the configuration data directly to the data capture device via a wireless connection.

9. The computer program product of claim 7, wherein transmitting the configuration data to the data capture device of the subject comprises transmitting the configuration data to a computer, wherein the configuration data updates the software application of the data capture device during a subsequent update facilitated by the computer.

10. The computer program product of claim 7, wherein defining the engagement degree of the subject comprises:

calculating, for each of the fragments having an identified perception, a product of the weight of the identified perception and the frequency of the perception identified in the fragments; and calculating the engagement degree as a sum of the products for all of the fragments having identified perceptions.

11. The computer program product of claim 7, wherein the program instructions executable by the processor to cause the processor to generate the classification for each of the perceptions further causes the processor to annotate a corpus comprising the electronic texts.

12. The computer program product of claim 7, wherein a plurality of the perceptions are classified as a negative perception, wherein calculating the score for each of a plurality of strategies of engagement classified as being related to the at least one negative perception further comprises:

ranking each of the negative perceptions according to a multiplication of the respective perception weight by the respective perception frequency; and calculating the score for each of the plurality of strategies of engagement classified as being related to the at least one negative perception, according to a sum of the rankings.

* * * * *